(12) United States Patent
Costa

(10) Patent No.: US 6,616,643 B1
(45) Date of Patent: Sep. 9, 2003

(54) ABSORBENT ARTICLE

(75) Inventor: Rogerio Costa, Lorena-SP (BR)

(73) Assignee: Johnson & Johnson Industria E Comercio LTDA (BR)

( * ) Notice: Subject to any disclaimer, the term of this patent is extended or adjusted under 35 U.S.C. 154(b) by 0 days.

(21) Appl. No.: 09/532,238

(22) Filed: Mar. 22, 2000

(30) Foreign Application Priority Data

Apr. 7, 1999 (BR) ............................................. 99010470

(51) Int. Cl.[7] ................................................ A61F 13/15
(52) U.S. Cl. ............................ 604/385.02; 604/385.04
(58) Field of Search ..................... 604/385.01–385.05; 206/438–440

(56) References Cited

U.S. PATENT DOCUMENTS

| | | |
|---|---|---|
| 3,886,941 A | 6/1975 | Duane et al. |
| 3,920,019 A | 11/1975 | Schaar |
| 6,015,934 A | 1/2000 | Lee et al. |
| 6,168,582 B1 * | 1/2001 | Hasegawa .............. 604/385.03 |

FOREIGN PATENT DOCUMENTS

| | | |
|---|---|---|
| EP | 0688549 A2 | 12/1995 |
| GB | 2142242 A | 1/1985 |
| GB | 2194878 A | 3/1988 |
| SE | 504 514 C2 | 2/1997 |

OTHER PUBLICATIONS

European Search Report (Appln. No. EP 00 30 2911).

* cited by examiner

Primary Examiner—Aaron J. Lewis
Assistant Examiner—C L Anderson

(57) ABSTRACT

The present invention relates to an individually folded and wrapped product, comprising and absorbent article and an enveloping sheet. The absorbent article is provided with side flaps and adhesive regions that aid in fixing it to a wearer's panties, keeping it in the correct position and avoiding the occurrence of leakage. The enveloping sheet totally encloses the absorbent article when the absorbent article is transversely folded over itself with the flaps in an open position.

1 Claim, 3 Drawing Sheets

ABSORBENT ARTICLE

BACKGROUND OF THE INVENTION

The present invention relates to an absorbent article such as a sanitary napkin, an absorbent article for urinary incontinence and the like, said absorbent article being preferably disposable and provided with side tabs with adhesive regions that aid in fixing said absorbent article to the wearer's panties, maintaining it in the correct position and avoiding the occurrence of leakage.

Particularly, the present invention relates to an absorbent article associated with an enveloping sheet suitable for accommodating and enclosing said absorbent before and after its use.

As known from the prior art, absorbent articles are generally disposable and used for collecting and holding vaginal exudates, especially menstrual blood, intermenstrual secretions and also urine in the cases of incontinence.

Typically, such absorbent articles comprise a body of absorbent material, generally planar and elongate in shape, surrounded by a permeable front layer, suitable for entering in contact with the wearer's body, and an impermeable back layer in contact with her panties.

The permeable front layer is adapted for entering into contact with the wearer's pelvic region and, in general, it is made of a soft and non-irritating material. According to the present state of the art, this layer may be made of a perforated plastic film, a porous or reticulate foam, a sheet of woven or non-woven material with natural fibers (wood or cotton fibers), artificial fibers (polyester or polypropylene fibers), or else a combination of synthetic or natural fibers.

Said front layer may be of a hydrophobic material, in order to have a tendency to remain dry.

On the other hand, said impermeable back layer has the function of preventing the absorbed and held fluid from passing to the clothes or skin of the wearer, being optionally manufactured from a sheet of polyethylene. Said back layer may be permeable to vapors and, in this case, ft is either provided with small pores or made of a non-woven liquid-impermeable material.

The absorbent articles of the prior art usually have one or more adhesive regions on the surface of the respective impermeable back layers, especially in a central portion in the longitudinal and/or transverse direction thereof, in order to fix the absorbent articles in the inner part of the crotch region of the panties. Said adhesive region may be shaped as a single strip, multiple strips, in a spiral, with stitches or any adequate configuration, and there is a tendency to apply the adhesive to said back layer along one or more longitudinal strips for the sake of processing ease.

Said absorbent body, in turn, may be made from any material capable of absorbing and holding bodily exudates, such as for example wood pulp, bamboo fibers, sugar-cane bagasse, corncob or corn stem, turf moss, absorbent foams or sponges, synthetic or polymeric fibers, superabsorbent materials (which form hydrogels when they enter in contact with liquids), combinations of the above materials and others.

At present, many of the feminine intimate absorbent articles have flexible flaps extending to the sides, for instance, as an extension of one or both of said front and back layers, or still separate from these layers, but associated with the absorbent article. Said flaps serve to fix said absorbent article to the panties, and for this purpose they bend over the edges of the crotch portion of the panties, over the outer layer thereof. Preferably, one of more regions of such flaps have areas coated with adhesives permitting one to secure them to the panties, thus minimizing the displacement of the absorbent article when in use.

Said adhesive regions are preferably located on the back surface of the flaps corresponding, for instance, to an extension of the impermeable back layer of the absorbent article. As known from the prior art, some feminine absorbent articles, such as some designed for night-time use, are longer and have more than one flap on each side of the product, that is to say, each side of the absorbent article has two different flaps, the absorbent article having therefore four flaps. This type of product is also included in the present invention.

Adhesive-coated areas, either on the impermeable back layer of the absorbent article or on the respective flaps, should be protected against any kind of contact before the absorbent article is used, in order to avoid impairing the adhesion power of said regions or causing them to stick in an undesirable manner to the absorbent article or clothes of the wearer, in which case the handling of the absorbent article becomes difficult and eventually inadequate.

For this purpose, protection sheets are traditionally used, which are also known as "release papers," comprised of a sheet of paper covered with a layer of silicone or antiadherent resin facing the adhesive surface. Said protection sheets are used on the absorbent article prior to use.

Aiming at the comfort of the wearer, absorbent articles have been individually folded and wrapped, so that they can be carried separately and discreetly. However, known individually folded and wrapped products are not very practical, since they require several steps to release the absorbent article from its envelope and fix the absorbent article to the wearer's panties. Usually said steps involve handling said front and back layers of the absorbent article, thus impairing the hygiene of the absorbent article, which will be in close contact with the pelvic region of the wearer.

Another problem encountered with conventional individually folded and wrapped products is that, after the absorbent article has been released from said envelope, the flaps still remain fixed to each other or to the absorbent body itself. It is then necessary to release these flaps so as to make them available for use.

One of the objectives of the present invention is to provide an individually folded and wrapped product comprising an enveloping sheet suitable for accommodating and enveloping an absorbent article, the enveloping sheet being shaped and folded so as to allow also the wearer to release the absorbent article from the sheet in a single step and, consequently, have minimum contact with the front layer of the absorbent article. This objective is achieved by means of an individually folded and wrapped product comprising 1) and absorbent article comprising a liquid-permeable front layer, a liquid-impermeable back layer comprising adhesive regions, an absorbent body arranged between the front and back layers, and flaps extending laterally from the napkin, and 2) an enveloping sheet, characterized in that said enveloping sheet totally encloses the absorbent article when the absorbent article is transversely folded over itself with the flaps in an open position.

In the prior art there are individually folded and wrapped products similar to that of the invention. However, in the prior art products, the flaps are folded over the absorbent body into a closed position, and only then is the absorbent article enclosed by the enveloping sheet. Such embodiments require great design complexity in locating protection sheets over the adhesive regions, and in folding the absorbent article. According to the present invention, the enclosure of the absorbent article occurs with the side flaps open (regardless of number of flaps, e.g., at least one flap). Assembly of the individually folded and wrapped product is much easier. In addition, opening of the envelope and retrieval of the absorbent article is also easier. The enveloping sheet of this invention tends to be larger than those of the prior art, and for this reason it is more effectively used for disposing used articles.

DESCRIPTION OF THE DRAWINGS

The present invention will now be described in greater detail with reference to the accompanying drawings, in which.

DETAILED DESCRIPTION OF THE FIGURES

Figure 1:
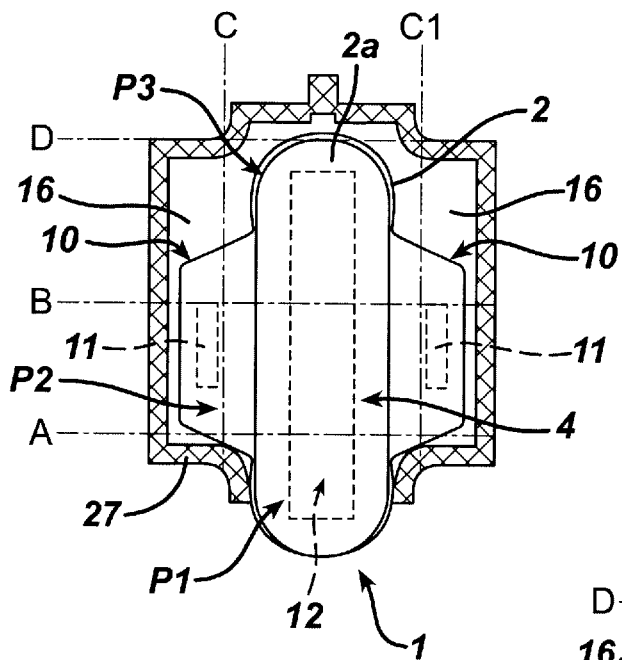
FIG. 1 is a front view of an absorbent article fixed to an enveloping sheet, according to a preferred embodiment of the present invention.

As illustrated in FIGS. 1–7 and 10, the individually folded and wrapped product 1 comprises an absorbent article 2 comprising a substantially planar absorbent body 2a, enveloped by a permeable front layer 4, suitable for entering in close contact with the pelvic region of the wearer and by an impermeable back layer 5 facing the respective panties (not shown).

Figure 10:
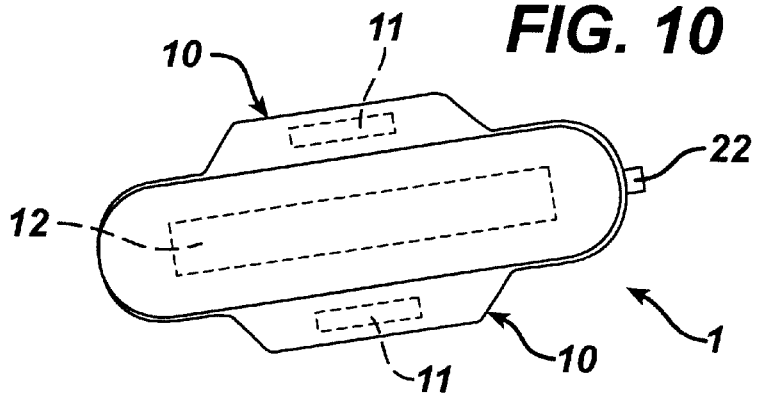
FIG. 10 is a perspective view of the absorbent article detached from the enveloping sheet of FIGS. 8 and 9.

Said absorbent article 2 further comprises flexible flaps 10, which extend laterally as an extension of the front layer 4, back layer 5, or both, or else a separate component attached to the absorbent article 2. In the example described, the absorbent article 2 has only two flaps 10, but it could have 4 or more of them. As illustrated in FIG. 10, each of the back faces of these flaps 10 has a first adhesive region 11 allowing one to fix it to the crotch portion of the panties. A second adhesive region 12 is provided in a longitudinally central portion of the back layer 5 of the absorbent article 2.

The material used as adhesive regions 11 and 12 is known to those skilled in the art, being usually a pressure sensitive adhesive. As already described, this material is applied in the form of a single strip, multiple strips, points or any other adequate configuration.

According to the present invention, an enveloping sheet 16 is provided, which should be conformed to be larger than the dimensions of the absorbent article 2, that is to say, it should be capable of accommodating and enclosing the absorbent article 2 before or after use, so as to obtain a package which prevents the leakage of any fluid retained in the absorbent article 2. In other words, the enveloping sheet 16 may be as long as or longer than the absorbent article 2.

Figure 2:
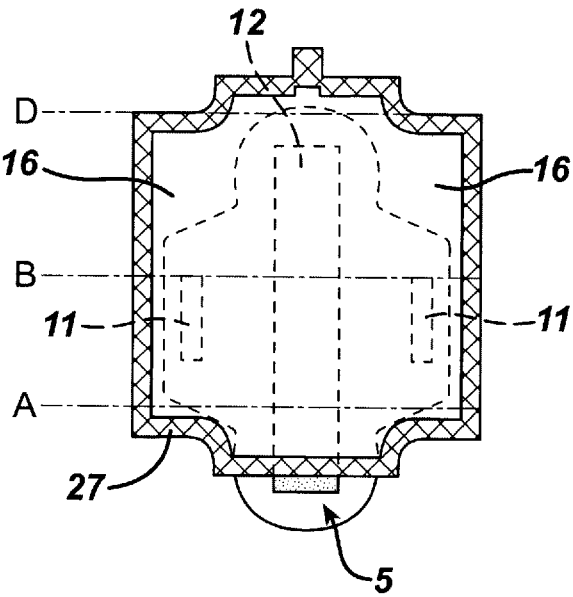
FIG. 2 is a rear view of the absorbent article and enveloping sheet as illustrated in FIG. 1.
Figure 3:
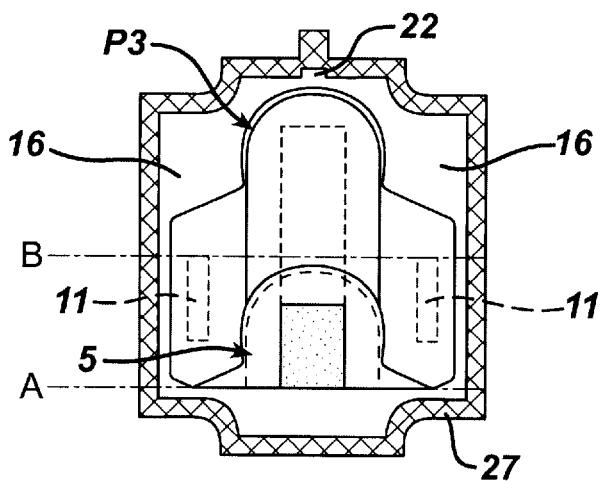
FIG. 3 is a front view of the absorbent article illustrated in FIG. 1, partly folded along a first transverse fold line.
Figure 4:
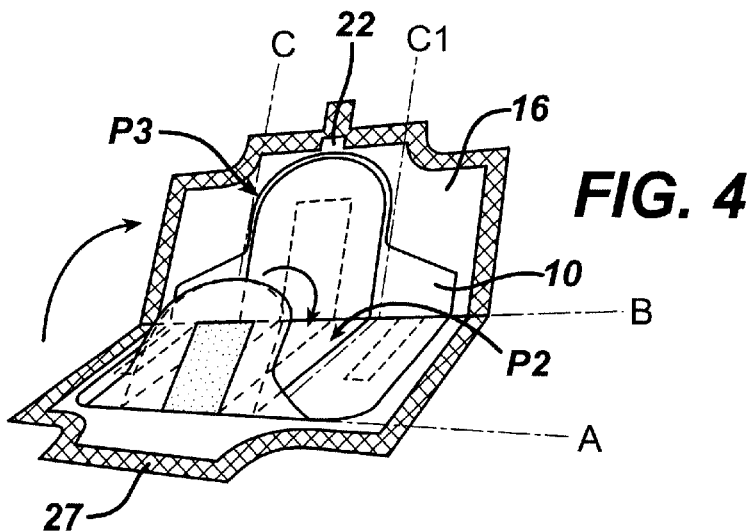
FIG. 4 is a perspective view of the absorbent article and enveloping sheet of FIG. 1 being further folded along a second transverse fold line.

As can be seen from FIGS. 1 and 2, the enveloping sheet 16 has a shape that follows the contour of the absorbent article 2, an end portion of the absorbent article 2 defined by panel P1 projecting beyond the edge 27 of the sheet 16 when said absorbent article 2 is unfolded. The enveloping sheet 16, may be manufactured from one or more layers, being preferably manufactured from an impermeable and flexible material, so that it can be folded around the absorbent article 2, and it may be a plastic film, paper, non-woven fabric, any of these materials being coated with at least some kind of resin, such as, for instance, an antiadherent, laminate, or a combination of these materials. Preferably, the sheet 16 is made from a thin impermeable plastic film such as polyethylene. As can be seen from FIGS. 1–9, the edge 27 may be reinforced by a process of gripping the material, and said edge 27 may still be glued or soldered by heating when a material suitable for such process is used.

Figure 8:
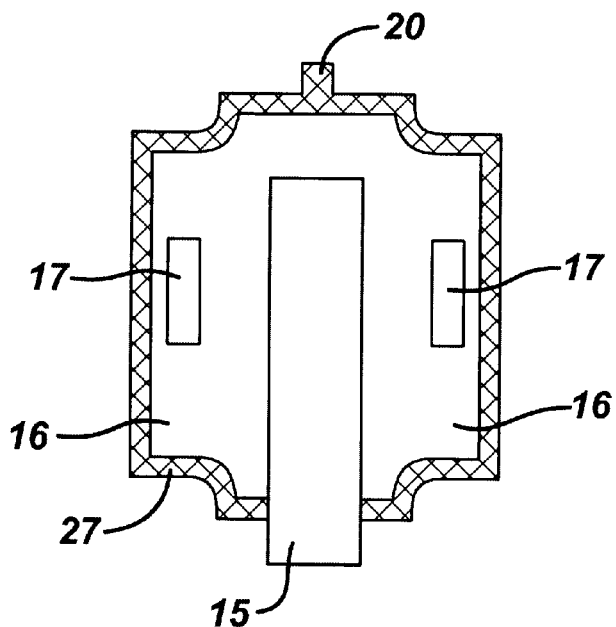
FIG. 8 is a front view of an enveloping sheet with protection sheets.
Figure 9:
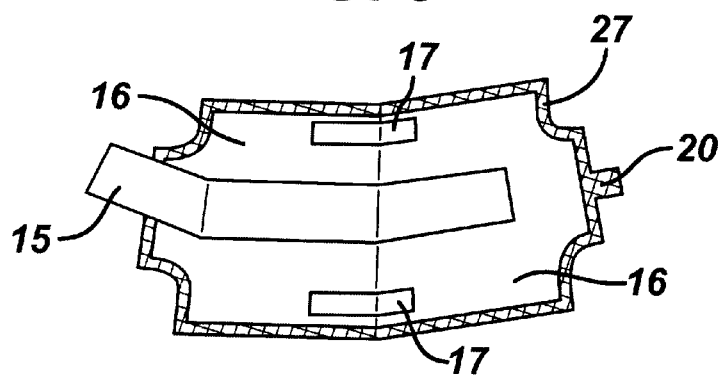
FIG. 9 is a perspective view of the enveloping sheet illustrated in FIG. 8.

As illustrated in FIGS. 8 and 9, the enveloping sheet 16 is provided with protection sheets 15 and 17, longitudinally positioned. Protection sheets 17 are suitable for temporarily protecting the adhesive regions 11, and a protection sheet 15 is positioned in the central region of the enveloping sheet 16 for temporarily protecting the second adhesive regions 12.

As known in the art, protection sheets 15 and 17 should provide a temporary adhesion to the adhesive regions 11 and 12, so that the latter will not lose adhesion to the panties.

According to the invention, the protection sheets 15 and 17 have two opposed faces, one that protects or adheres releasably or temporarily to the adhesive regions 12 and 11, respectively, and the other which adheres definitively or nonreleasably to the enveloping sheet 16.

When the absorbent article 2 is fixed to the enveloping sheet 16, the back layer 5 remains in contact with said sheet 16 (see FIG. 1).

In order for the enveloping sheet 16 to enclose the absorbent article 2 totally, fold lines are provided on the absorbent article 2, the flaps 10 and the enveloping sheet 16. These fold lines may be understood as lines along which a fold is formed, since the adjacent material is flexible and makes it possible to form a fold without there being a physically defined line.

Figure 6:
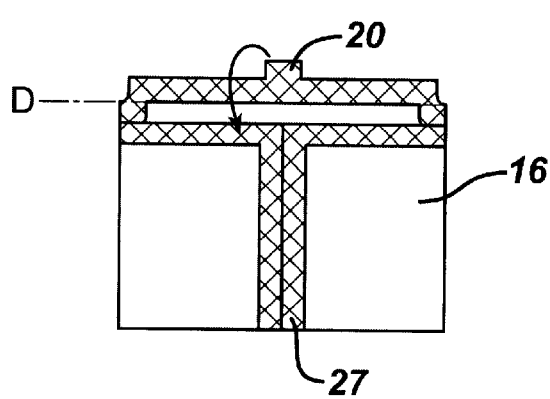
FIG. 6 is a front view of the absorbent article and enveloping sheet of FIG. 5 fully folded along the longitudinal fold lines.
Figure 7:
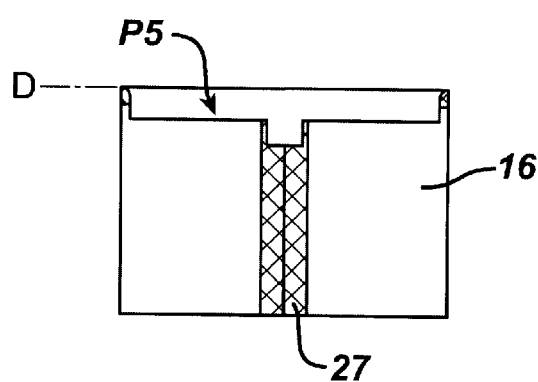
FIG. 7 is a front view of an individually folded and wrapped product of the invention.

As shown in FIGS. 1–4, the individually folded and wrapped product comprises a first transverse fold line A, along which the lower portion of the absorbent article 2 is folded. Along a second transverse fold line B, a middle portion of the absorbent article 2 and the enveloping sheet 16 are folded together. Longitudinal fold lines C and C1 are provided on the flaps 10 of the absorbent article 2 and the enveloping sheet 16 so that the absorbent article 2 and the enveloping sheet 16 may be folded together along the longitudinal fold lines. Finally, as shown in FIGS. 6 and 7, a third transverse fold line D is provided at the top end of the enveloping sheet 16.

As used herein, the terms "transverse" and "longitudinal" refer to directions parallel to the major and minor axes of the absorbent article. Transverse refers to a direction parallel to the minor axis of the absorbent article. Longitudinal refers to a direction parallel to the major axis of the absorbent article.

Figure 5:
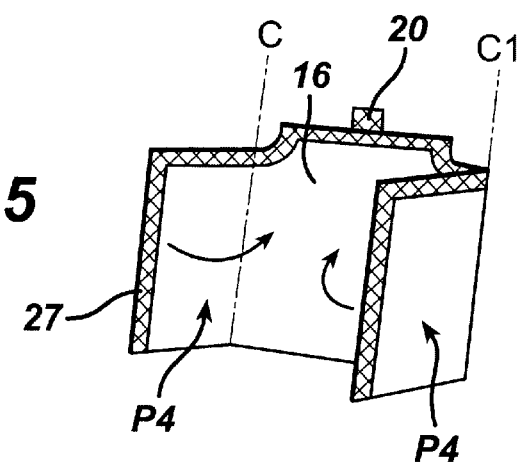
FIG. 5 is a perspective view of the absorbent article and enveloping sheet of FIG. 4 being further folded along longitudinal fold lines.

The individually folded and wrapped product is formed by folding the absorbent article inside the enveloping sheet as follows. Referring to FIGS. 1, 5, and 6, panels P1, P2, and P3 have approximately and preferably the same longitudinal length. Panel P1 comprising only the absorbent article 2 is defined by the lower end portion of the absorbent article 2 and by the first transverse fold line A. Panel P2 comprising both the absorbent article 2 and the enveloping sheet 16 is defined by the first and second transverse fold lines A and B.

Panel P3 comprising the absorbent article 2 and the sheet 16 is defined by the upper end portions of the absorbent article 2 and the sheet 16 and by second transverse fold line B.

As shown in FIG. 5, fourth panel P4 comprises two parts defined by two longitudinal side portions of the enveloping sheet 16 and longitudinal fold lines C and C1. Panel P4 includes the flaps 10 and the enveloping sheet 10.

A fifth panel P5 comprises only the enveloping sheet 16 and is defined by the top end portion of the sheet 16 and by the third transverse fold line D.

The steps of folding the absorbent article 2 and the enveloping sheet 16 into the individually folded and wrapped product are shown in FIGS. 3–7. First, in FIG. 3 and 4, panel P1 is folded on the first transverse fold line A in order to cover panel P2 partly (see FIG. 3). Next, panel P3 is folded along transverse fold line B, covering panel P1 already folded in the preceding step and causing the absorbent article 2 to become totally covered by the sheet 16 with flaps 10 in an open or unfolded position.

As illustrated in FIG. 5, panels P4 may optionally be folded along longitudinal fold lines C and C1 (see also FIG. 6). Finally, panel P5 may optionally by folded along the third transverse fold line D, causing the sheet 16 to enclose the absorbent article 2 further (see also FIG. 7).

Optionally, the enveloping sheet 16 may be provided with a projection 20 at the top end thereof, and this projection 20 may also comprise an adhesive surface suitable for adhering panel P5 during the final step of folding the absorbent article 2 in conjunction with the sheet 16.

It is important to mention that the invention includes other embodiments in which the absorbent article is longer than that illustrated in the Figure and/or includes additional flaps. As such, the absorbent article may be folded additional times over itself, and once it is enclosed in the enveloping sheet, it can be folded more times, longitudinally and/or transversely, in order to acquire a smaller volume, if desired.

When there is the need for carrying individually folded and wrapped products, the wearer can do so in her bag, for instance, without impairing the hygiene of said absorbent article, since the latter is protected by the enveloping sheet.

When the wearer needs to use the absorbent article, she can unfold the enveloping sheet by following these steps. If the enveloping sheet 16 is provided with a projection 20, the wearer can first release the latter. Once the projection 20 has been released, the wearer unfolds the panels P5 and then the panels P4.

By opening panels P3 and P1 afterwards, the absorbent article 2 will remain available to be released from the sheet 16 (see FIG. 1). At this point, the absorbent article 2 remains fixed to the sheet 16 by the adhesive regions 11 and 12, which are fixed to the protection sheets 17 and 15.

Optionally, in order for the absorbent article 2 to be released from said sheet 16, a tab 22 may be provided, fixed to the impermeable back layer, or at any other point of the upper end portion of the absorbent article 2. Said tab 22 may be made of any material whatever, for example, non-woven fabric, plastics, paper, combinations thereof, etc., in the form of a strip, strap, or any other that enables the wearer to pull the absorbent article 2 out of the enveloping sheet 16. Using tab 22 the wearer can release the absorbent article 2 from the sheet 16 with a single movement and have minimum contact with the permeable front layer 4, whereby the latter remains clean. The wearer can also release the absorbent article 2 from the sheet 16 through the panel P1, which is not fixed directly to said sheet 16.

When the absorbent article 2 is separated from the enveloping sheet 16, protection sheets 15 and 17 remain fixed to the sheet 16, exposing the adhesive regions 11 and 12 to be glued to the panties. This is in contrast with conventional products, in which flaps remain fixed to each other or to the body of the absorbent article itself, which requires an additional release step and causes the wearer to enter in contact with the front layer, thus impairing the hygiene of the absorbent article.

After releasing the absorbent article from the sheet, the wearer can keep said sheet for disposal of the absorbent article after it has been used. Since the enveloping sheet is manufactured from an impermeable material, the absorbent article may be enclosed in it even after use, without the risk of leakage of fluid contained in the absorbent body.

Said tab 22 can be used by the wearer to release the absorbent article from the panties right after use of the absorbent article, and also as an aid for handling the latter and throwing it away, or else for helping enclose the absorbent article in the enveloping sheet.

A preferred embodiment having been described, it should be understood that the scope of the present invention embraces other possible variations.

What is claimed is:

1. A individually folded and wrapped product comprising:
   (1) an absorbent article comprising
      a liquid-permeable front layer;
      a liquid-impermeable back layer comprising adhesive regions thereon;
      an absorbent body arranged between the front and the back layers; and
      at least one flap extending laterally;
   (2) an enveloping sheet;
   wherein said enveloping sheet totally encloses the absorbent article when the absorbent article is transversely folded over itself with the at least one flap in an open position; and
   (3) a first transverse fold line along which a lower portion of the absorbent article is folded,
   (4) a second transverse fold line along which a middle portion of the absorbent article and the enveloping sheet are jointly folded,
   (5) a longitudinal fold line along which the at least one flap and the enveloping sheet are jointly folded, and
   (6) a third transverse fold line along which a top portion of the enveloping sheet is folded.

* * * * *